United States Patent
Li et al.

(10) Patent No.: US 9,144,793 B2
(45) Date of Patent: Sep. 29, 2015

(54) CARRIER FOR SILVER CATALYST, ITS PREPARATION, A SILVER CATALYST MADE FROM THE SAME AND ITS USE

(75) Inventors: Jinbing Li, Beijing (CN); Xianfeng Li, Beijing (CN); Wei Lin, Beijing (CN); Qiang Lin, Beijing (CN); Jianshe Chen, Beijing (CN); Zhixiang Zhang, Beijing (CN); Shuyuan Cao, Beijing (CN); Shujuan Wang, Beijieng (CN); Wujun Dai, Beijing (CN)

(73) Assignees: China Petroleum & Chemical Corporation, Beijing (CN); Beijing Research Institute of Chemical Industry, China Petroleum & Chemical Corporation, Beijing (CN)

(*) Notice: Subject to any disclaimer, the term of this patent is extended or adjusted under 35 U.S.C. 154(b) by 684 days.

(21) Appl. No.: 13/339,272

(22) Filed: Dec. 28, 2011

(65) Prior Publication Data

US 2012/0172608 A1 Jul. 5, 2012

(30) Foreign Application Priority Data

Dec. 29, 2010 (CN) .......................... 2010 1 0622856

(51) Int. Cl.
| | | |
|---|---|---|
| *B01J 29/06* | (2006.01) | |
| *C07D 301/03* | (2006.01) | |
| *B01J 29/89* | (2006.01) | |
| *B01J 29/03* | (2006.01) | |
| *B01J 21/04* | (2006.01) | |
| *B01J 23/66* | (2006.01) | |
| *B01J 37/00* | (2006.01) | |
| *B01J 35/10* | (2006.01) | |
| *C07D 301/10* | (2006.01) | |
| *B01J 35/02* | (2006.01) | |

(52) U.S. Cl.
CPC .................. *B01J 29/89* (2013.01); *B01J 21/04* (2013.01); *B01J 23/66* (2013.01); *B01J 29/0308* (2013.01); *B01J 29/0325* (2013.01); *B01J 35/1009* (2013.01); *B01J 35/1038* (2013.01); *B01J 37/0009* (2013.01); *C07D 301/03* (2013.01); *B01J 35/026* (2013.01); *B01J 35/1042* (2013.01); *B01J 2229/20* (2013.01); *B01J 2229/42* (2013.01); *C07D 301/10* (2013.01)

(58) Field of Classification Search
USPC ............ 502/60, 63, 64, 71, 77, 242; 549/536, 549/534
See application file for complete search history.

(56) References Cited

U.S. PATENT DOCUMENTS

| | | | |
|---|---|---|---|
| 4,994,588 A | 2/1991 | Kapicak et al. | |
| 5,733,842 A | 3/1998 | Gerdes et al. | |
| 2005/0010074 A1* | 1/2005 | Iwayama et al. | 585/481 |
| 2007/0093669 A1 | 4/2007 | Le-Khae et al. | |
| 2007/0173655 A1 | 7/2007 | Grey | |
| 2008/0039316 A1* | 2/2008 | Bhise et al. | 502/347 |
| 2009/0177000 A1 | 7/2009 | Natal et al. | |
| 2010/0056816 A1* | 3/2010 | Wallin et al. | 549/534 |

FOREIGN PATENT DOCUMENTS

| | | |
|---|---|---|
| CN | 1400048 A | 3/2003 |
| CN | 1400053 A | 3/2003 |
| CN | 1511632 A | 7/2004 |
| CN | 101007287 A | 8/2007 |
| CN | 101850243 A | 10/2010 |
| EP | 0207550 A1 | 1/1987 |

* cited by examiner

*Primary Examiner* — Elizabeth Wood
(74) *Attorney, Agent, or Firm* — Novick, Kim & Lee, PLLC; Allen Xue (57) ABSTRACT

The present invention discloses an alumina carrier for a silver catalyst, a process for preparing the alumina carrier, a silver catalyst made from the alumina carrier, and a use of the silver catalyst in the production of ethylene oxide by the oxidization of ethylene. The alumina carrier comprises alumina and promoters, as well as titanium silicate molecular sieve(s); and therefore, has an improved catalytic activity.

21 Claims, 2 Drawing Sheets

CARRIER FOR SILVER CATALYST, ITS PREPARATION, A SILVER CATALYST MADE FROM THE SAME AND ITS USE

FIELD OF THE INVENTION

The present invention relates to a carrier for a silver catalyst, its preparation and its use. Specifically, the present invention relates to an alumina carrier for silver catalyst, a process for preparing said alumina carrier, a silver catalyst made from said alumina carrier, and a use of said silver catalyst in the production of ethylene oxide by the oxidization of ethylene. The alumina carrier contains not only alumina and promoters, but also titanium silicate molecular sieve(s), and therefore has an improved catalytic activity.

BACKGROUND OF THE INVENTION

Ethylene is oxidized under the action of the silver catalyst to mainly produce ethylene oxide, which is accompanied by the side reaction to produce carbon dioxide and water. The main properties of the silver catalyst include activity, selectivity and stability. The activity is reflected by the reaction temperature at which ethylene oxide is produced with a certain reaction load. The lower the reaction temperature is, the higher the catalyst activity is. The selectivity means the ratio of the mole of ethylene that converts to ethylene oxide to the total mole of ethylene that takes part in the reaction. The stability is reflected by the rate at which the activity or selectivity drops. The lower the dropping rate is, the better the catalyst stability is.

The silver catalyst having high activity, high selectivity and good stability during the production of ethylene oxide by the oxidization of ethylene can improve the economical benefit remarkably. Thus, it is a main research object of the silver catalyst to make a silver catalyst having high activity, high selectivity and good stability.

The silver catalyst preparation method in the prior art comprises the steps of preparing porous carrier such as alumina and applying active components and promoters onto said porous carrier.

Some new silver catalyst carrier technologies are reported in recent years; for example, see the Chinese patent application publication Nos. CN1511632A, CN1400048A and CN1400053A.

SUMMARY OF THE INVENTION

The present inventors have made deep researches in the field of the silver catalyst and its alumina carrier, and surprisingly found that the addition of titanium silicate molecular sieve during the preparation of the alumina carrier for silver catalyst can improve the pore structure and strength of the resulting carrier. The silver catalyst made from said carrier can have an improved epoxidation ability and activity for the oxidation of ethylene to ethylene oxide.

Therefore, an object of the present invention is to provide an alumina carrier and a preparation for the same. The silver catalyst, derived from said carrier or the carrier made from said preparation, can have an improved epoxidation ability and activity for the oxidation of ethylene to ethylene oxide.

Another object of the present invention is to provide a silver catalyst prepared from the above-mentioned carrier.

Another object of the present invention is to provide a use of the above-mentioned silver catalyst in the oxidation of ethylene to ethylene oxide.

Specifically, the present invention provides the following technical solutions.

Solution 1

An alpha-alumina carrier, wherein said alpha-alumina carrier is modified with at least one titanium silicate molecular sieve, preferably TS-series, ETS-series, T-MCM-series, and T-SBA-series, more preferably TS-1, TS-2, ETS-10, ETS-4, T-MCM-41, and T-SBA-15, further more preferably TS-1, ETS-10 or a mixture thereof.

Solution 2

The alpha-alumina carrier of Solution 1, which is characterized in that the titanium-to-aluminum mass ratio in the carrier is 0.00003-0.07, and the titanium-to-silicon atom ratio on the carrier surface is 0.0001-0.33.

Solution 3

The alpha-alumina carrier of Solution 1, which is characterized in that in case that said alpha-alumina carrier is modified with at least one TS-series, the titanium-to-silicon atom ratio on the carrier surface is 0.0001-0.02, and in case that said alpha-alumina carrier is modified with at least one ETS-series, the titanium-to-silicon atom ratio on the carrier surface is 0.20-0.33.

Solution 4

The alpha-alumina carrier according to any one of Solution 1-3, wherein said alpha-alumina carrier has one or more properties of:

(1) a specific surface of $0.2$-$2.0$ $m^2/g$,
(2) a pore volume of $0.35$-$0.85$ ml/g,
(3) a water absorption of $\geq 30\%$,
(4) a side crashing strength of 20-120N/particle,
(5) an alpha-alumina content of 70 wt % or more, based on the total weight of the alpha-alumina carrier.

Solution 5

A process for preparing an alpha-alumina carrier, comprises the steps of (I) preparing a mixture of:
(a) based on the total weight of the solids in the mixture, 50-90 wt % of alpha-alumina trihydrate of 50-500 meshes;
(b) based on the total weight of the solids in the mixture, 5-50 wt % of pseudo-boehmite of $\geq 200$ meshes;
(c) based on the total weight of the solids in the mixture, 0-1.5 wt % of heavy alkaline-earth metal compound;
(d) based on the total weight of the solids in the mixture, 0.1-3.0 wt % of fluoride mineralizing agent;
(e) based on the total weight of the solids in the mixture, 1-15 wt % of titanium silicate molecular sieve;
(f) based on the total weight of components (a) to (e), 15-60 wt % of binder; and
(g) an appropriate amount of water;
wherein the total weight of the solids in the mixture means the total weight of components (a), (b), (c), (d) and (e), and the total amount of all solid components in the above mixture is 100% by weight;

(II) kneading the mixture obtained in the step (I) homogenously and extruding into shape to give shaped bodies; and (III) drying the shaped bodies obtained in the step (II), and then calcining them to the alpha-alumina carrier.

Solution 6

The process of Solution 5, wherein said fluoride mineralizing agent is one or more of hydrogen fluoride, aluminum fluoride, ammonium fluoride, magnesium fluoride and cryolite.

Solution 7

The process of Solution 5, wherein said heavy alkaline-earth metal compound is one or more of oxides, sulfates, acetates, nitrates, and oxalates of strontium and barium, preferably barium oxide, barium sulfate, barium nitrate, barium carbonate or a mixture thereof.

Solution 8

The process of Solution 5, wherein said titanium silicate molecular sieve is one or more of TS-series, ETS-series, T-MCM-series, and T-SBA-series, preferably TS-1, TS-2, ETS-10, ETS-4, T-MCM-41, and T-SBA-15, more preferably TS-1, ETS-10 or a mixture thereof.

Solution 9

The process of Solution 5, wherein said binder is an acid.

Solution 10

The process of Solution 9, wherein the acid and pseudo-boehmite are partially or completely replaced by alumina sol.

Solution 11

The process of Solution 9, wherein said acid is an aqueous nitric acid solution, wherein the weight ratio of nitric acid to water is 1:1.25-1:10, preferably 1:2-1:4.

Solution 12

The process of Solution 5, wherein in the step (III), the calcination temperature is 1000° C.-1500° C., preferably 1000° C.-1400° C., and/or the calcination time is 2-24 hours.

Solution 13

The process of Solution 5, wherein in the step (I), based on the total weight of the solids in the mixture prepared in the step (I), the amount of component (a) is 65-80 wt %, the amount of component (b) is 10-20 wt %, the amount of component (c) is 0.1-1.0 wt %, the amount of component (d) is 1.0-2.0 wt %, and the amount of component (e) is 4-9 wt %, and/or the amount of component (f) is 15-20 wt % based on the total weight of components (a) to (e), wherein the total weight of the solids in the mixture means the total weight of components (a), (b), (c), (d) and (e), the total amount of all solid components in the above mixture is 100% by weight.

Solution 14

A silver catalyst useful in the oxidation of ethylene to ethylene oxide, which is prepared by the method comprising the steps of:

(1) Impregnating the alpha-alumina carrier according to any one of Solutions 1-4 or impregnating the alpha-alumina carrier prepared by the process according to any one of Solutions 5-13 with a solution containing sufficient amounts of a silver compound, an organic amine, an optional alkali metal promoter, an optional alkaline-earth metal promoter, and an optional rhenium promoter and optionally its co-promoter;

(2) Filtering the impregnation solution; and (3) Activating the carrier obtained in the step (2) in an oxygen-containing gas to produce the silver catalyst.

Solution 15

The silver catalyst according to Solution 14, wherein the silver compound is silver oxide, silver nitrate and/or silver oxalate, and the silver compound is used in such an amount that measured on silver atom, silver is present in the silver catalyst in an amount of 1-40%, preferably 5-25%, based on the total weight of the silver catalyst.

Solution 16

The silver catalyst according to Solution 14, wherein said alkali metal promoter is one or more of lithium, sodium, potassium, rubidium and cesium compounds, preferably cesium sulfate, cesium nitrate, lithium nitrate and/or potassium hydroxide, especially preferably cesium sulfate, and the alkali metal promoter is used in such an amount that measured on alkali metal atom, the alkali metal promoter is present in the silver catalyst in an amount of 0-2000 ppm, preferably 5-2000 ppm, more preferably 5-1500 ppm by weight, based on the total weight of the silver catalyst.

Solution 17

The silver catalyst according to Solution 14, wherein the alkaline-earth metal promoter is one or more of magnesium, calcium, strontium and barium compounds, such as one or more of oxides, oxalates, sulfates, acetates and nitrates of magnesium, calcium, strontium and barium, and the alkaline-earth metal promoter is used in such an amount that measured on alkaline-earth metal atom, the alkaline-earth metal promoter is present in the silver catalyst in an amount of 0-10000 ppm, preferably 0-8000 ppm by weight, based on the total weight of the silver catalyst.

Solution 18

The silver catalyst according to Solution 14, wherein the rhenium promoter is one or more of rhenium oxides, perrhenic acid, cesium perrhenate and ammonium perrhenate, preferably ammonium perrhenate, and the rhenium promoter is used in such an amount that measured on rhenium atom, the rhenium promoter is present in the silver catalyst in an amount of 0-2000 ppm, preferably 10-2000 ppm, more preferably 100-1000 ppm by weight, based on the total weight of the silver catalyst.

Solution 19

The silver catalyst according to Solution 14, wherein the organic amine is pyridine, butyl amine, ethylene diamine, 1,3-propylene diamine, ethanolamine or a mixture thereof, preferably a mixture of ethylene diamine and ethanolamine.

Solution 20

The silver catalyst according to Solution 14, wherein the activation in the step (3) is conducted in air or a nitrogen-oxygen mixed gas with oxygen content of 21 vol % or less.

Solution 21

The silver catalyst according to Solution 14, the activation in the step (3) is conducted at a temperature of 180-700° C., preferably 200-500° C., and/or the activation time in the step (3) is 1-120 mins, preferably 2-60 mins.

Solution 22

A process for producing ethylene oxide by ethylene oxidation, wherein the silver catalyst according to any one of Solutions 14-21 is used.

These aspects and other objects, features and advantages of the present invention will be more apparent upon reading the specification.

DETAILED DESCRIPTION

The alpha-alumina carrier of the present invention is an alpha-alumina carrier modified with titanium silicate molecular sieve(s). Said carrier can be used to produce ethylene oxide by ethylene oxidation. In some embodiments, titanium-to-aluminum mass ratio in the carrier is 0.00003-0.07. In some embodiments, titanium-to-aluminum mass ratio in the carrier is 0.0001-0.05. In some embodiments, titanium-to-aluminum mass ratio in the carrier is 0.001-0.04. In some embodiments, titanium-to-aluminum mass ratio in the carrier is 0.002-0.04. In some embodiments, titanium-to-silicon atom ratio on the carrier surface is 0.0001-0.33. In some embodiments, titanium-to-silicon atom ratio on the carrier surface is 0.0001-0.02. In some embodiments, titanium-to-silicon atom ratio on the carrier surface is 0.02-0.1. In some embodiments, titanium-to-silicon atom ratio on the carrier surface is 0.1-0.33. In some embodiments, titanium-to-silicon atom ratio on the carrier surface is 0.2-0.33. In some embodiments, said carrier is modified with at least one TS-series, and the titanium-to-silicon atom ratio on the carrier surface is 0.0001-0.02. In some embodiments, said carrier is modified with at least one ETS-series and the titanium-to-silicon atom ratio on the carrier surface is 0.20-0.33.

The present alpha-alumina carrier modified with titanium silicate molecular sieve(s) has one or more properties of
(1) a specific surface of 0.2-2.0 m$^2$/g,
(2) a pore volume of 0.35-0.85 ml/g,
(3) a water absorption of 30%,
(4) a side crashing strength of 20-120N/particle, and
(5) an alpha-alumina content of 70 wt % or more, based on the total weight of the alpha-alumina carrier.

It is necessary for the preparation of the alpha-alumina carrier of the present invention to use the alpha-alumina trihydrate, i.e., component (a). The alpha-alumina trihydrate is granular and has a particle size of 50-500 meshes, e.g., 200-500 meshes. Based on the total weight of the solids in the mixture prepared in the step (I), alpha-alumina trihydrate is usually used in an amount of 50-90 wt %, such as 65-80 wt %, e.g., 73-77 wt %.

It is also necessary for the preparation of the alpha-alumina carrier of the present invention to use the pseudo-boehmite, i.e., component (b). The pseudo-boehmite is granular and has a particle size of ≥200 meshes, such as ≥250 meshes, e.g. 200-400 meshes. Based on the total weight of the solids in the mixture prepared in the step (I), pseudo-boehmite as component (b) is usually used in an amount of 5-50 wt %, such as 10-20 wt %, e.g., 14-16 wt %.

In the preparation of the alpha-alumina carrier of the present invention, the heavy alkaline-earth metal compound, i.e., component (c) can be optionally used in the step (I). The heavy alkaline-earth metal compound is strontium and barium compounds, such as oxide, sulfate, acetate, nitrate and oxalate of strontium and/or barium. In some embodiments, barium oxide, barium sulfate, barium nitrate, barium carbonate or a mixture thereof is used as the heavy alkaline-earth metal compound. Based on the total weight of the solids in the mixture prepared in the step (I), the heavy alkaline-earth metal compound is added in an amount of 0-1.5 wt %, such as 0.1-1.0 wt %, e.g., 0.1-0.5 wt %.

In the preparation of the alpha-alumina carrier of the present invention, the fluoride mineralizing agent is added as component (d) so as to accelerate the alumina crystal form conversion. The fluoride used in the present invention is an inorganic fluoride, comprising hydrogen fluoride, ammonium fluoride, aluminum fluoride, magnesium fluoride, cryolite and the like, such as one or more of hydrogen fluoride, aluminum fluoride, ammonium fluoride, magnesium fluoride and cryolite, e.g., ammonium fluoride. For the purpose of the present invention, based on the total weight of the solids in the mixture prepared in the step (I), the fluoride mineralizing agent is added in an amount of 0.1-3.0 wt %, such as 1.0-2.0 wt %.

In the preparation of the alpha-alumina carrier of the present invention, it is further necessary to add at least one titanium silicate molecular sieve as component (e). The titanium silicate molecular sieve can be of TS-series, ETS-series, molecular sieves obtained by introducing Ti atoms into pure silicon molecular sieve (e.g., T-MCM-series, T-SBA-series), such as one or more of TS-1, TS-2, ETS-10, ETS-4, T-MCM-41 and T-SBA-15, e.g., TS-1, ETS-10 or a mixture thereof. For the purpose of the present invention, based on the total weight of the solids in the mixture prepared in the step (I), the titanium silicate molecular sieve is added in an amount of 1-15 wt %, such as 3-10 wt %, e.g., 4-9 wt % or 6-9 wt %.

In the preparation of the alpha-alumina carrier of the present invention, a binder can be added as component (f). The binder and pseudo-boehmite in the mixture form an alumina sol, which bind components in the mixture together to form an extrudable paste. The binder comprises an acid, such as nitric acid, formic acid, acetic acid, propionic acid, hydrochloric acid and the like. Alternatively, the acid and pseudo-boehmite can be partially or completely replaced by alumina sol. In case of using the acid as binder, it is preferable to use an aqueous nitric acid solution, wherein the weight ratio of nitric acid to water is 1:1.25-1:10, preferably 1:2-1:4. For the purpose of the present invention, the binder is usually added in an amount of, based on the total weight of components (a) to (e), 15-60 wt %, such as 15-20 wt %.

In a preferable embodiment for the preparation of the alpha-alumina carrier of the present invention, based on the total weight of the solids in the mixture prepared in the step (I), the amount of component (a) is 65-80 wt %, the amount of component (b) is 10-20 wt %, the amount of component (c) is 0.1-1.0 wt %, the amount of component (d) is 1.0-2.0 wt %, and the amount of component (e) is 4-9 wt %, and/or the amount of component (f) is 15-20 wt % based on the total weight of components (a) to (e), wherein the total weight of the solids in the mixture means the total weight of components (a), (b), (c), (d) and (e), the total amount of all solid components in the above mixture is 100% by weight.

After kneading the mixture obtained in the step (I) homogenously, in general, a paste is obtained. It is usually advantageous for the present invention to firstly mix components (a), (b), (c) (if any), (d) and (e) homogenously and charge into the kneader, and then add components (f) and (g) to knead into a paste, in particular an extrudable paste. The obtained paste is shaped, particularly by extrusion to produce shaped bodies. The shaped bodies can be dried to a moisture content of 10 wt % or less. The drying temperature can be 80-120° C. The drying time can be controlled depending on the moisture content, for example, the drying time is 1-24 hours. The obtained shaped bodies can be in a form of ring, sphere, column or multihole column or the like.

After drying, the shaped bodies are generally calcined at a temperature of 1000° C.-1500° C., such as 1000° C.-1400° C. for not less than 1 hour, e.g. 2-24 hours, such as 2-8 hours. Substantially all of alumina, for example, more than 90% of alumina can be converted to alpha-alumina by the calcination so as to obtain the alpha-alumina carrier.

Thus, according to another aspect of the present invention, the alpha-alumina carrier prepared by the above-mentioned process is provided, wherein said carrier has the following characteristics: a specific surface of 0.2-2.0 m$^2$/g, a pore volume of 0.35-0.85 ml/g, a water absorption of ≥30%, (4) a side crashing strength of 20-120N/particle, and an alpha-alumina content of 70 wt % or more, based on the total weight of the alpha-alumina carrier.

According to the present invention, the specific surface area of the carrier is measured according to the International Standard ISO-9277 by the Nitrogen Gas Physical Adsorption BET Method. For example, the specific surface area of the carrier can be measured with Nitrogen Gas Physical Adsorption Instrument NOVA2000e (Quantachrome Corp., USA).

The pore volume of the carrier is measured by the mercury porosimetry. For example, the pore volume of the carrier can be measured with AutoPore9510-type Mercury Porosimeter (Micromeritics Instrument Corp., USA).

The content of the alkaline-earth metal in the carrier can be obtained by calculation or measurement (for example, X-Ray fluorescence).

The side crashing strength of the carrier, for example, can be measured with the DL II type Particle Strength Tester (manufactured by Dalian Research and Design Institute of Chemical Industry) by randomly selecting thirty carrier sample particles, measuring the side crashing strength for each particle, and then calculating the average of the side crashing strength.

The water-absorption of the carrier means the volume of water which is absorbed in saturation by a unit mass of the carrier and is expressed as mL/g. The water-absorption can be determined by weighing a certain amount of the carrier (assuming its mass as m1), boiling the carrier in the boiling water for 1 hour, removing the carrier from the boiling water, keeping the carrier upright on a wet gauze having a suitable water content to remove the redundant water from the carrier, finally weighing the water-absorbing carrier (assuming its mass as m2), and calculating the water-absorption according to the following formula:

Water absorption=$(m2-m1)/m1/\rho_{water}$, wherein an $\rho_{water}$ is the water density at the measuring temperature under atmospheric pressure.

The titanium-to-silicon (Ti/Si) atom ratio on the carrier surface is measured on a PHI Quantera SXM photoelectron spectrometer using Al Kα radiation (hv=1486.6 eV), wherein all measured values of binding energies (BE) are referred to the C1s line at 284.8 eV.

The titanium-to-aluminum (Ti/Al) mass ratio in the carrier is measured by a Rigaku ZSX-100 e X-ray fluorescence (XRF) spectrometer.

The alpha-alumina carrier produced by the process for preparing the alumina carrier according to the present invention can be in a conventional form in the art, such as ring, sphere, column, multihole column or the like.

After obtaining the alpha-alumina carrier of the present invention, a silver catalyst can be produced in a manner known by the skilled person in the art or in a conventional manner. For example, the silver catalyst of the present invention can be produced by impregnating the above alumina carrier with a solution containing a silver compound and an organic amine.

Thus, according to another aspect of the present invention, a silver catalyst useful in the oxidation of ethylene to ethylene oxide is provided, which silver catalyst is prepared by the method comprising the steps of:

(1) Impregnating the above-mentioned alpha-alumina carrier with a solution containing sufficient amounts of a silver compound, an organic amine, an optional alkali metal promoter, an optional alkaline-earth metal promoter, and an optional rhenium promoter and optionally its co-promoter;

(2) Filtering the impregnation solution; and (3) Activating the carrier obtained in the step (2) in an oxygen-containing gas to produce the silver catalyst.

The above silver compound can be any silver compound suitable for preparing the silver catalyst useful for the production of ethylene oxide. According to the present invention, silver oxide, silver nitrate and/or silver oxalate can be used. The amount of the silver compound used in the impregnation procedure should be sufficient so that the finally produced silver catalyst contains 1-40 wt %, such as 5-25 wt % of silver measured on the silver atom based on the total weight of the silver catalyst.

The above organic amine compound can be any organic amine compound suitable for preparing the silver catalyst useful for the production of ethylene oxide, provided that the organic amine compound has an ability to form a silver-amine complex with the silver compound. For the purpose of the present invention, pyridine, butyl amine, ethylene diamine, 1,3-propylene diamine, ethanolamine or a mixture thereof, such as a mixture of ethylene diamine and ethanolamine can be used.

In the method for preparing the silver catalyst of the present invention, the optionally used alkali metal promoter can be lithium, sodium, potassium, rubidium or cesium compound (such as nitrate, sulfate and hydroxide) or a mixture thereof. In some embodiments, the alkali metal promoter is one or more selected from lithium, potassium and cesium compound, such as cesium sulfate, cesium nitrate, lithium nitrate and/or potassium hydroxide. In some embodiments, the alkali metal promoter is cesium sulfate. In some embodiments, the alkali metal promoter is added to the impregnation solution in such an amount that the alkali metal is present in the final catalyst in an amount of 0-2000 ppm, such as 5-2000 ppm or 5-1500 ppm by weight, measured on the alkali metal atom.

In the method for preparing the silver catalyst of the present invention, the optionally used alkaline-earth metal promoter can be one or more of magnesium, calcium, strontium and barium compound, such as oxide, oxalate, sulfate, acetate and nitrate. In some embodiments, the optionally used alkaline-earth metal promoter can be barium and/or strontium compound, such as barium acetate and/or strontium acetate. In some embodiments, the alkaline-earth metal aid is added to the impregnation solution in such an amount that the alkaline-earth metal is present in the final catalyst in an amount of 0-10000 ppm, such as 0-8000 ppm by weight, measured on the alkaline-earth metal atom.

In the method for preparing the silver catalyst of the present invention, the optionally used rhenium promoter can be rhenium oxides, perrhenic acid, perrhenates, or a mixture thereof. In some embodiments, the optionally used rhenium promoter is perrhenic acid and perrhenates, such as perrhenic acid, cesium perrhenate, ammonium perrhenate or any mixture thereof, especially ammonium perrhenate. In some embodiments, the rhenium promoter is added to the impregnation solution in such an amount that the rhenium metal is present in the final catalyst in an amount of 0-2000 ppm, preferably 10-2000 ppm, more preferably 100-1000 ppm by weight, measured on the rhenium metal atom.

In case that the impregnation solution contains the rhenium promoter, a co-promoter of the rhenium promoter can be added so as to further improve the activity, the selectivity and the stability of the obtained silver catalyst. The co-promoter of the rhenium promoter according to the present invention can be a compound of any transitional metal in the Periodic Table, or a mixture of transitional metal compounds, such as an oxyacid of an element selected from Groups VIB and VIIB, and a salt thereof, for example, tungstenic acid, sodium tungstate, potassium tungstate, ammonium tungstate, cesium tungstate, molybdic acid, ammonium molybdate, ammonium metatungstate. In some embodiments, the co-promoter of the rhenium promoter is used in such an amount that the co-promoter of the rhenium promoter is present in the final catalyst in an amount of 0-1000 ppm, such as 0-500 ppm by weight, measured on the weight of active element.

For the purpose of the impregnation of step (1), it is favorable to impregnate the alumina carrier below an atmosphere pressure, such as under an absolute pressure of below 10 mmHg. The impregnation is usually conducted for 10-60 minutes. After filtering, the carrier obtained in the step (2) is activated in an oxygen-containing gas, i.e., the step (3) is conducted to produce the silver catalyst. The activation in the step (3) is favorably conducted in air or a nitrogen-oxygen mixed gas with oxygen content of 21 vol % or less; the activation temperature is usually 180-700° C., such as 200-500° C., and the activation time is usually 1-120 mins, such as 2-60 mins.

A silver catalyst can be obtained by the method for preparing the silver catalyst of the present invention, and shows an improved epoxidation ability and activity for the oxidation of ethylene to ethylene oxide.

Thus, the present invention also relates to a use of the silver catalyst according to the present invention in the production of ethylene oxide by oxidation of ethylene.

EXAMPLES

The present invention will be illustrated by the following examples, but the scope of the present invention is not limit thereto.

The Catalyst Performance Evaluation

The silver catalysts used in the examples of the present invention were tested in the laboratory micro-reactor for the catalytic reaction performance and the stability. In the micro-reactor testing apparatus, the reactor was a stainless steel reaction tube having an inner diameter of 4 mm. The reaction tube was disposed in a heating jacket. The loading volume of the catalyst was 1 mL. The inert filler was disposed in the lower portion so that the catalyst bed was located in the constant temperature area of the heating jacket.

The standard evaluation conditions for the catalytic activity and the selectivity used in the present invention are as follows:

The composition of the reaction gas (mol %):

| | |
|---|---|
| Ethylene ($C_2H_4$) | 28.0 ± 1.0 |
| Oxygen ($O_2$) | 7.4 ± 0.2 |
| Carbon dioxide ($CO_2$) | <3.0 |
| Ballast gas($N_2$) | Balance |
| Inhibitor 1,2-dichloroethane | 0.1 ppm-2.0 ppm |
| Reaction pressure | 2.1 MPa |
| Space velocity | 7000/h |
| The concentration of ethylene oxide (EO) in the effluent from the reactor | 2.5 mol % |
| Space-time yield | 342 g EO/mlCat./h |

Under a certain space velocity, when the reaction becomes stable and reaches the above reaction conditions, the compositions of the gases at the inlet and the outlet of the reactor are continually measured. The measurement results, after applying the volume-shrinkage correction thereto, are used to calculate the selectivity according to the following formula:

$$S = \frac{\Delta EO}{\Delta EO + 0.5 \times \Delta CO_2} \times 100\%$$

wherein $\Delta EO$ is the ethylene oxide concentration difference between the outlet and the inlet of the reactor; and $\Delta CO2$ is the carbon dioxide concentration difference between the outlet and the inlet of the reactor. Ten or more sets of experiment data are taken and averaged as the experiment result of that day.

The Preparation for Carrier

Example 1

Figure 1:
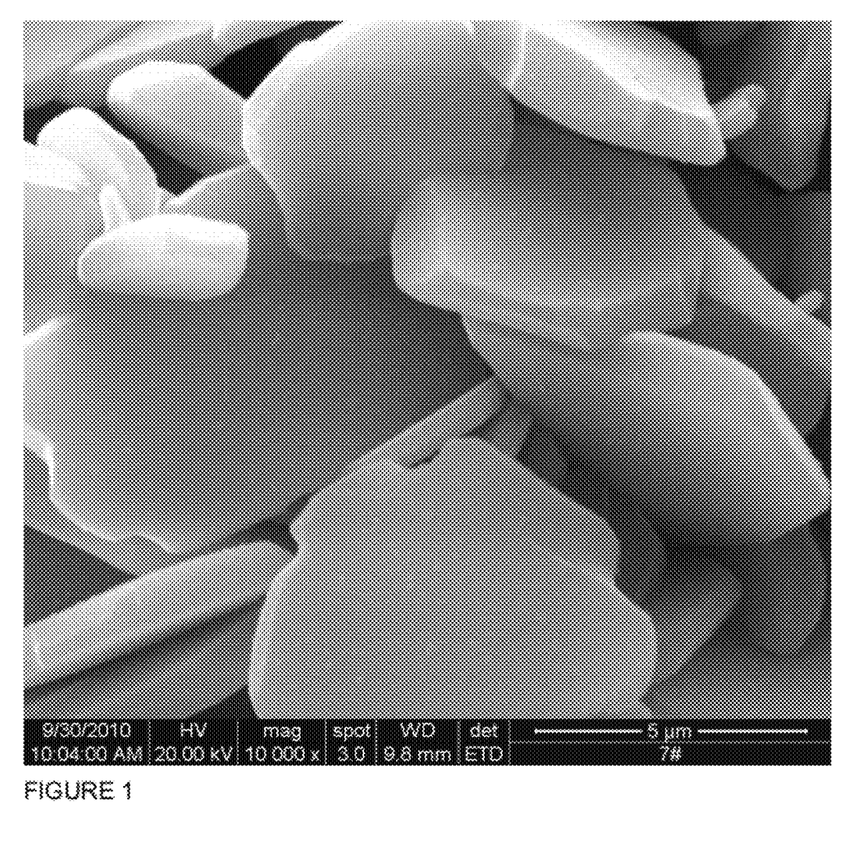
FIG. 1 shows a scanning electron microscope for the carrier prepared in Example 1.

403 g of alpha-alumina trihydrate (200-500 meshes), 81 g of pseudo-boehmite (200-400 meshes), 7 g of NH4F and 1.0 g of BaSO4 were placed into a mixer to mix homogenously, transferred into a kneader, then added a diluted nitric acid aqueous solution (nitric acid:water=1:3 by weight, 90 mL), kneaded to an extrudable paste, and extruded into shape to give five-hole cylinder bodies with an outer diameter of 8.0 mm, a length of 6.0 mm and an inner diameter of 1.0 mm. The cylinder bodies were dried at 80-120° C. for 10 hours, and the free water content was decreased to below 10 wt %. The resulting dried cylinder bodies were placed in an electric furnace and heated up during a course of 30 hours from room temperature (about 25° C.) to 1400° C., and kept at that temperature constantly for 2 hours to obtain a white alpha-alumina carrier, which was named as Z-1. The scanning electron microscope of the carrier Z-1 was shown in FIG. 1.

Example 2

Figure 2:
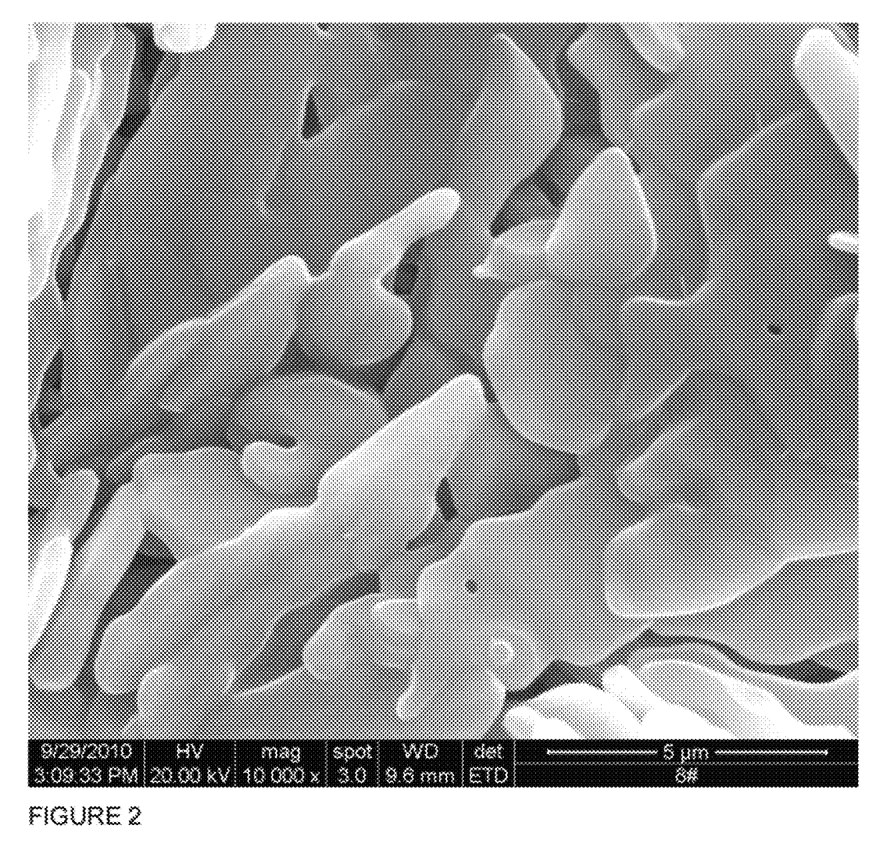
FIG. 2 shows a scanning electron microscope for the carrier prepared in Example 2.

379 g of alpha-alumina trihydrate (200-500 meshes), 76 g of pseudo-boehmite (200-400 meshes), 30 g of TS-1 (obtained from China University of Petroleum, Beijing), 7 g of NH4F and 1.0 g of BaSO4 were placed into a mixer to mix homogenously, transferred into a kneader, then added a diluted nitric acid aqueous solution (nitric acid:water=1:3 by weight, 84 mL), kneaded to an extrudable paste, and extruded into shape to give five-hole cylinder bodies with an outer diameter of 8.0 mm, a length of 6.0 mm and an inner diameter of 1.0 mm. The cylinder bodies were dried at 80-120° C. for 10 hours, and the free water content was decreased to below 10 wt %. The resulting dried cylinder bodies were placed in an electric furnace and heated up during a course of 30 hours from room temperature to 1400° C., and kept at that temperature constantly for 2 hours to obtain a white alpha-alumina carrier, which was named as Z-2. The scanning electron microscope of the carrier Z-2 was shown in FIG. 2.

Example 3

367 g of alpha-alumina trihydrate (200-500 meshes), 74 g of pseudo-boehmite (200-400 meshes), 44 g of TS-1 (obtained from China University of Petroleum, Beijing), 7 g of NH4F and 1.0 g of BaSO4 were placed into a mixer to mix homogenously, transferred into a kneader, then added a diluted nitric acid aqueous solution (nitric acid:water=1:3 by weight, 83 mL), kneaded to an extrudable paste, and extruded into shape to give five-hole cylinder bodies with an outer diameter of 8.0 mm, a length of 6.0 mm and an inner diameter of 1.0 mm. The cylinder bodies were dried at 80-120° C. for 10 hours, and the free water content was decreased to below 10 wt %. The resulting dried cylinder bodies were placed in an electric furnace and heated up during a course of 30 hours from room temperature to 1400° C., and kept at that temperature constantly for 2 hours to obtain a white alpha-alumina carrier, which was named as Z-3.

Example 4

379 g of alpha-alumina trihydrate (200-500 meshes), 76 g of pseudo-boehmite (200-400 meshes), 30 g of ETS-10 (obtained from China University of Petroleum, Beijing), 7 g of $NH_4F$ and 1.0 g of $BaSO_4$ were placed into a mixer to mix homogenously, transferred into a kneader, then added a diluted nitric acid aqueous solution (nitric acid:water=1:3 by weight, 84 mL), kneaded to an extrudable paste, and extruded into shape to give five-hole cylinder bodies with an outer diameter of 8.0 mm, a length of 6.0 mm and an inner diameter of 1.0 mm. The cylinder bodies were dried at 80-120° C. for 10 hours, and the free water content was decreased to below 10 wt %. The resulting dried cylinder bodies were placed in an electric furnace and heated up during a course of 30 hours from room temperature to 1400° C., and kept at that temperature constantly for 2 hours to obtain a white alpha-alumina carrier, which was named as Z-4.

Example 5

367 g of alpha-alumina trihydrate (200-500 meshes), 74 g of pseudo-boehmite (200-400 meshes), 44 g of ETS-10 (obtained from China University of Petroleum, Beijing), 7 g of NH4F and 1.0 g of BaSO4 were placed into a mixer to mix homogenously, transferred into a kneader, then added a diluted nitric acid aqueous solution (nitric acid:water=1:3 by weight, 83 mL), kneaded to an extrudable paste, and extruded into shape to give five-hole cylinder bodies with an outer diameter of 8.0 mm, a length of 6.0 mm and an inner diameter of 1.0 mm. The cylinder bodies were dried at 80-120° C. for 10 hours, and the free water content was decreased to below 10 wt %. The resulting dried cylinder bodies were placed in an electric furnace and heated up during a course of 30 hours from room temperature to 1400° C., and kept at that temperature constantly for 2 hours to obtain a white alpha-alumina carrier, which was named as Z-5.

The carriers described in Examples 1-5 were measured respectively for side crashing strength, water absorption, specific surface area, pore volume, alkaline-earth metal content in the carrier, Ti/Si atom ratio and Ti/Al mass ratio. The results were shown in Table 1.

TABLE 1

The physical properties of Examples 1-5

| | Carrier | | | | |
|---|---|---|---|---|---|
| | Z-1 | Z-2 | Z-3 | Z-4 | Z-5 |
| Side Crashing Strength(N/particle) | 79 | 83 | 85 | 84 | 87 |
| Water Absorption(%) | 56 | 37 | 34 | 39 | 35 |
| Specific Surface Area(m2/g) | 1.32 | 1.23 | 1.20 | 1.25 | 1.21 |
| Pore Volume(mL/g) | 0.52 | 0.48 | 0.45 | 0.49 | 0.45 |
| Ba Content (wt %) | 0.11 | 0.11 | 0.11 | 0.11 | 0.11 |
| Ti/Si Atom Ratio | — | 0.0005 | 0.0182 | 0.21 | 0.31 |
| Ti/Al Mass Ratio | 0 | 0.0022 | 0.0033 | 0.024 | 0.036 |

The Preparation for Catalysts

Example 6

700 g of silver nitrate was dissolved into 750 ml of deionized water to give a first solution. 325 g ammonium oxalate was dissolved into 250 ml of deionized water at 50° C. to give a second solution. These two solutions were mixed under a violent stirring to form a white silver oxalate precipitate, aged for 1 hour, and filtered. The filter cake was washed with deionized water until no nitrate group ion was in the filtrate to give a silver oxalate pasty filter cake containing about 60 wt % of silver and about 15% of water.

To a glass flask with a stirrer were added 300 g ethylene diamine, 110 g ethanolamine and 375 g deionized water to give a mixed solution. The prepared pasty silver oxalate was slowly added to the mixed solution while stirring. The solution temperature was maintained at a temperature between −5° C. and 10° C., and silver oxalate was dissolved completely. Then 2.2 g cesium sulfate and 1.4 g strontium acetate were added. Deionized water was further added so that the solution reached 2000 g to give an impregnation solution for use. The impregnation solution had a silver content of 22 wt %.

100 g of the carrier Z-1 prepared in Example 1 was placed into a glass vessel which can be vacuumed. The vessel was vacuumed to an absolute pressure below 10 mmHg, and into the vessel was poured the above formulated impregnation solution until the carrier was immersed, maintained for 30 mins, filtered to remove the redundant solution, then heated in an air stream at 350° C. for 5 mins, and cooled to give a Silver Catalyst named as CZ-1.

Example 7

Example 6 was repeated, except that 100 g carrier Z-1 was replaced by 100 g carrier Z-2 to give a Silver Catalyst named as CZ-2.

Example 8

Example 6 was repeated, except that 100 g carrier Z-1 was replaced by 100 g carrier Z-3 to give a Silver Catalyst named as CZ-3.

Example 9

Example 6 was repeated, except that 100 g carrier Z-1 was replaced by 100 g carrier Z-4 to give a Silver Catalyst named as CZ-4.

Example 10

Example 6 was repeated, except that 100 g carrier Z-1 was replaced by 100 g carrier Z-5 to give a Silver Catalyst named as CZ-5.

The catalysts CZ-1, CZ-2, CZ-3, CZ-4 and CZ-5 prepared in Examples 6-10 were respectively analyzed for the silver and promoter contents, wherein all of the contents were based on the metal elements. The results were shown in Table 2.

In addition, under the evaluation conditions given in the above section "The catalyst performance evaluation," the silver catalysts were evaluated for the activity and selectivity of the catalysts in the micro-reactor evaluation apparatus. The results were shown in Table 2.

In Table 2, the reaction temperature and the selectivity refer to the data on the sixth day of the reaction.

| Catalyst | Ag Content (wt %) | Cs content (ppmw) | Sr Content (ppmw) | Reaction Temperature (° C.) | EO (mol %) | Selectivity (%) |
|---|---|---|---|---|---|---|
| CZ-1 | 16.2 | 363 | 282 | 229 | 2.5 | 82.1 |
| CZ-2 | 15.9 | 361 | 279 | 219 | 2.5 | 82.3 |
| CZ-3 | 16.3 | 361 | 287 | 225 | 2.5 | 82.1 |
| CZ-4 | 16.3 | 362 | 285 | 220 | 2.5 | 82.2 |
| CZ-5 | 16.0 | 363 | 280 | 225 | 2.5 | 82.2 |

The invention claimed is:

1. A carrier comprising alpha-alumina and at least one titanium silicate molecular sieve selected from the group consisting of TS-series molecular sieves, ETS-series molecular sieves, Ti-MCM-series molecular sieves, Ti-SBA-series molecular sieves, TS-1 molecular sieve, TS-2 molecular sieve, ETS-10 molecular sieve, ETS-4 molecular sieve, Ti-MCM-41 molecular sieve, Ti-SBA-15 molecular sieve, and a combination thereof.

2. The carrier of claim 1, wherein a titanium-to-aluminum mass ratio in the carrier is between 0.00003 and 0.07, as determined using a x-ray fluorescence (XRF) spectrometer, and wherein the titanium-to-silicon atom ratio on a surface of the carrier is between 0.0001 and 0.33, as determined using a x-ray photoelectron spectrometer (XPS).

3. The carrier of claim 1, wherein:
when said carrier comprises at least one TS-series molecular sieve, a titanium-to-silicon atom ratio on a surface of the carrier is between 0.0001 and 0.02, as determined using a x-ray photoelectron spectrometer (XPS); and
when said carrier comprises at least one ETS-series molecular sieve, the titanium-to-silicon atom ratio on the surface of the carrier is between 0.20 and 0.33, as determined using a x-ray photoelectron spectrometer (XPS).

4. The carrier of claim 1, wherein said carrier has one or more of the following properties
(1) a specific surface of 0.2-2.0 m²/g,
(2) a pore volume of 0.35-0.85 ml/g,
(3) a water absorption capacity of 3%,
(4) a side crushing strength of 20-120N/particle, and
(5) an alpha-alumina content of 70 wt % or more, based on the total weight of the carrier.

5. A process for preparing a carrier of claim 1, comprising the steps of
(I) preparing a mixture comprising:
(a) an alpha-alumina trihydrate of 50-500 meshes at 50-90 wt %, based on the total weight of the solids in the mixture;
(b) a pseudo-boehmite of ≥200 meshes at 5-50 wt %, based on the total weight of the solids in the mixture;
(c) a heavy alkaline-earth metal compound at 0-1.5 wt %, based on the total weight of the solids in the mixture;
(d) a fluoride mineralizing agent at 0.1-3.0 wt %, based on the total weight of the solids in the mixture;
(e) a titanium silicate molecular sieve at 1-15 wt %, based on the total weight of the solids in the mixture;
(f) a binder at 15-60 wt %, based on the total weight of components (a) to (e); and
(g) an appropriate amount of water; wherein the total weight of the solids in the mixture means the total weight of components (a), (b), (c), (d) and (e), and the total amount of all solid components in the above mixture is 100% by weight;
(II) kneading the mixture obtained in the step (I) to produce a homogenous composition and extruding the homogenous composition into shape to give shaped bodies; and
(III) drying at least one of the shaped bodies obtained in the step (II), and then calcining it to form the carrier,
wherein said heavy alkaline-earth metal compound is selected from the group consisting of oxides, sulfates, acetates, nitrates, and oxalates of strontium and barium, and a mixture thereof.

6. The process of claim 5, wherein said fluoride mineralizing agent is selected from the group consisting of hydrogen fluoride, aluminum fluoride, ammonium fluoride, magnesium fluoride, cryolite and a combination thereof.

7. The process of claim 5, wherein said heavy alkaline-earth metal compound is selected from the group consisting of barium oxide, barium sulfate, barium nitrate, barium carbonate, and a mixture thereof.

8. The process of claim 5, wherein said binder is an acid.

9. The process of claim 8, wherein said acid is an aqueous nitric acid solution, and wherein the weight ratio of nitric acid to water is between 1:1.25-1:10.

10. The process of claim 5, wherein, in step (III), the calcination temperature is 1000° C.-1500° C. and the calcination time is 2-24 hours.

11. The process of claim 5, wherein the amount of component (a) is 65-80 wt %, the amount of component (b) is 10-20 wt %, the amount of component (c) is 0.1-1.0 wt %, the amount of component (d) is 1.0-2.0 wt %, and the amount of component (e) is 4-9 wt %, and/or the amount of component (f) is 15-20 wt % based on the total weight of components (a) to (e).

12. A method for preparing a silver catalyst, comprising the steps of:
(1) impregnating the carrier of claim 1 with a solution containing sufficient amounts of a silver compound, an organic amine, an optional alkali metal promoter, an optional alkaline-earth metal promoter, an optional rhenium promoter, and an optional co-promoter of the rhenium promoter;
(2) separating the solution from the carrier; and
(3) activating the carrier obtained in the step (2) in an oxygen-containing gas to produce the silver catalyst.

13. The method according to claim 12, wherein said silver compound is silver oxide, silver nitrate, silver oxalate, or a combination thereof, and said silver compound is used in an amount that measured on silver atom, silver is present in the silver catalyst in an amount of 1-40%, based on the total weight of the silver catalyst.

14. The method according to claim 12, wherein the solution comprises said alkali metal promoter, said alkali metal promoter is one or more of lithium, sodium, potassium, rubidium, or cesium compounds, and said alkali metal promoter is used in an amount that measured on alkali metal atom, said alkali metal promoter is present in the silver catalyst in an amount of 5-2000 ppm by weight, based on the total weight of the silver catalyst.

15. The method according to claim 12, wherein the solution comprises said alkali metal promoter, said alkaline-earth metal promoter is selected from the group consisting of a magnesium oxide, a magnesium oxalate, a magnesium sulfate, a magnesium acetate, a magnesium nitrate, a calcium oxide, a calcium oxalate, a calcium sulfate, a calcium acetate, a calcium nitrate, a strontium oxide, a strontium oxalate, a strontium sulfate, a strontium acetate, a strontium nitrate, a barium oxide, a barium oxalate, a barium sulfate, a barium acetate, a barium nitrate, and a combination thereof, and wherein said alkaline-earth metal promoter is used in an amount that, when measured by alkaline-earth metal atoms, said alkaline-earth metal promoter is present in the silver catalyst in an amount of less than 10000 ppm by weight, based on the total weight of the silver catalyst.

16. The method according to claim 12, wherein the solution comprises said rhenium promoter, said rhenium promoter is selected from the group consisting of a rhenium oxide, perrhenic acid, cesium perrhenate, ammonium perrhenate, and a combination thereof and wherein said rhenium promoter is used in an amount that, when measured by rhenium atoms, said rhenium promoter is present in the silver catalyst in an amount of less than 2000 ppm by weight, based on the total weight of the silver catalyst.

17. The method according to claim 12, wherein the organic amine is selected from the group consisting of pyridine, butyl amine, ethylene diamine, 1,3-propylene diamine, ethanolamine, or a combination thereof.

18. The method according to claim 12, wherein the activation in the step (3) is conducted in air or a nitrogen-oxygen mixed gas with oxygen content of 21 vol % or less.

19. The method according to claim 12, wherein activating step (3) is conducted at a temperature of 180-700° C. and the activation time is 1-120 mins.

20. A process for producing ethylene oxide by ethylene oxidation, comprising the steps of:
   producing a silver catalyst according to the method of claim 12; and
   carrying out an oxidation reaction of ethylene in presence of the silver catalyst.

21. The method according to claim 14, wherein said alkali metal promoter is present in the silver catalyst in an amount of 5-1500 ppm by weight, based on the total weight of the silver catalyst.

* * * * *